United States Patent [19]

van der Jagt

[11] Patent Number: Plant 6,060

[45] Date of Patent: Dec. 15, 1987

[54] CHRYSANTHEMUM NAMED 'RED REFLA'

[75] Inventor: Martinus van der Jagt, Ter Aar, Netherlands

[73] Assignee: Chrysanthemum Breeders Association, N.V., Netherlands Antilles

[21] Appl. No.: 781,991

[22] Filed: Sep. 30, 1985

[51] Int. Cl.[4] ..... A01H 5/00

[52] U.S. Cl. ..... Plt./74

[58] Field of Search ..... Plt. 74, 79

*Primary Examiner*—Robert E. Bagwill

*Attorney, Agent, or Firm*—Parkhurst & Oliff

[57] ABSTRACT

The present invention is a new and distinct variety of Chrysanthemum of large sized blooms and red color.

3 Drawing Figures

BACKGROUND OF THE INVENTION

The present invention comprises a new and distinct cultivar of Chrysanthemum plant which is a cross of unknown parents. The invention was discovered by Martinus van der Jagt in May 1984 at Parad sweg 88, Ter Aar, Holland. The invention has been asexually reproduced by cuttings at th same location. The new cultivar has been found to retain its distinctive characteristics through successive propagations.

BRIEF DESCRIPTION OF THE DRAWINGS

The present invention has a new and distinct variety of Chrysanthemum is shown in the accompanying drawings, the color being as nearly true as possible with color photographs of this type.

FIG. 1 shows the full bloom of the new cultivar.

FIG. 2 shows various stages of bloom of the new cultivar.

FIG. 3 shows the foliage and stem of the new cultivar.

DESCRIPTION OF THE INVENTION

This new variety of Chrysanthemum is of the botanical classification *Chrysanthemum morifolium* named 'Red Refla'. When grown in the vicinity of, Ter Aar, Holland, it has a response time of approximately 8½ weeks. This new variety produces large sized blooms of a red color with a green-yellow center having a 17 days performance. This new variety Chrysanthemum has been found to retain its distinctive characteristics throughout successive propagations and may be planted under greenhouse conditions in Holland from weeks 01 till 34.

The following is a description of the plant and characteristics that distinguish it over related known variety and its antecedents:

Bud:
- *Size.*—Medium.
- *Form.*—Flat top.
- *Color.*—Garnet brown RHS 00918/3.

Botanical classification: *Chrysanthemum morifolium.*

Bloom:
- *Size.*—Large.
- *Fully expanded.*—8–9½ cms.
- *Borne.*—Single.
- *Stems.*—Strong.
- *Form.*—Single/semi double.
- *Permanence.*—17 days.

Color:
- *Center of flower.*—Chartreuse green RHS 663.
- *Base of petals.*—Brick red RHS 016/1.
- *Inside of petals.*—Brick red RHS 016/1.
- *Reverse of petals.*—Yellow ochre RHS 07/3.
- *Outer petals.*—Brick red RHS 016/1.
- *Tonality from a distance.*—Large attractive dark orange/red flower with upstanding petals.
- *Discoloration.*—Some to fire red RHS 15/1.

Petals:
- *Texture.*—Upper/underside rough.
- *Number.*—38–42.
- *Arrangement.*—Much imbricated (two/three rows).
- *Persistence.*—Good. Petals only reflex some at the edge.
- *Fragrance.*—Chrysanthemum.

Reproductive organs:
- *Stamen.*—Normal.
- *Pollen.*—Some appear when blooming.
- *Styles.*—Columnar.
- *Length.*—Medium.
- *Stigmas.*—Normal. Yellow.
- *Ovaries.*—Enclosed in calyx.

Plant:
- *Form.*—Herbaceous.
- *Growth.*—Vigorous.
- *Height.*—Tall. Appr. 105 cms.
- *Peduncle.*—Strong.

Foliage:
- *Color.*—Dark green.
- *Size.*—Appr. 11×6 cms.
- *Quantity.*—Normal to less.
- *Shape.*—Pointed.
- *Texture.*—Upperside rough. Underside smooth.
- *Ribs and Veins.*—Not clearly marked at upper side. Prominent at underside.
- *Edge.*—Deep undulated.
- *Leaf underside.*—Smooth.

In the description above color references are made to The Horticultural Color Chart I & II issued by the British Colour Council in collaboration with The Royal Horticultural Society, Copyright Robert F. Wilson, Vol I, 1938; Vol II, 1941, printed by Henry Stone & Son LTD., Banbury, England.

I claim:

1. A new and distinctive variety of Chrysanthemum as described and illustrated in the foregoing specification and accompanying drawings.

* * * * *

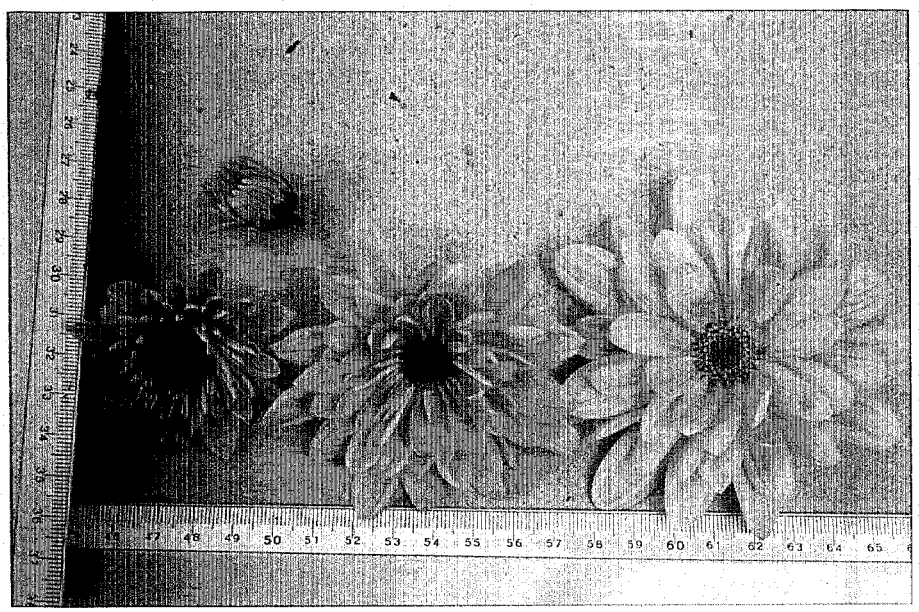

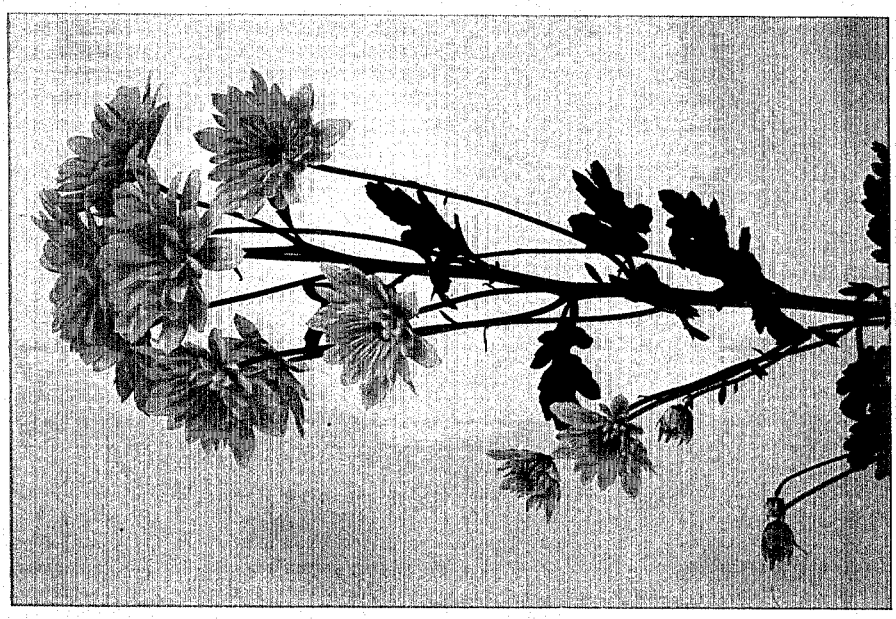
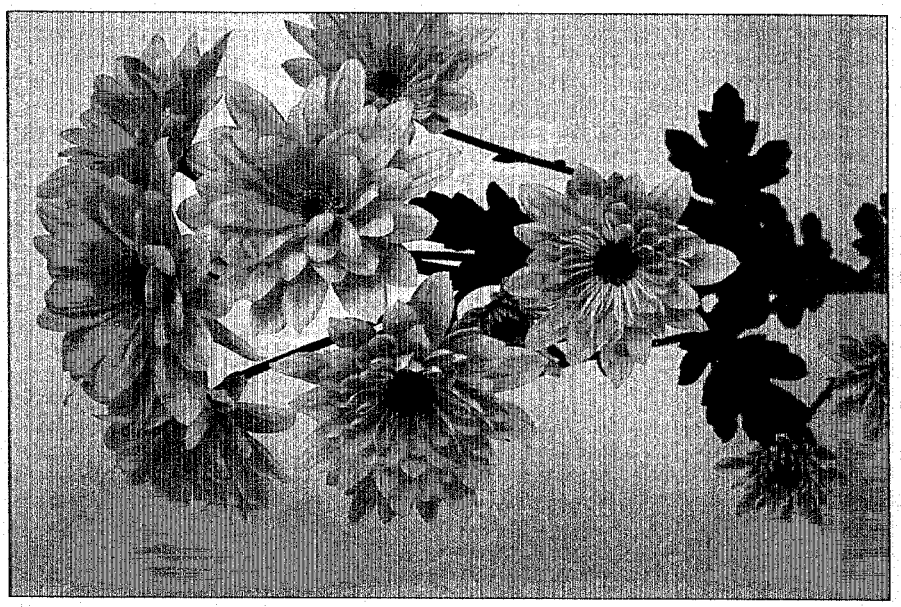

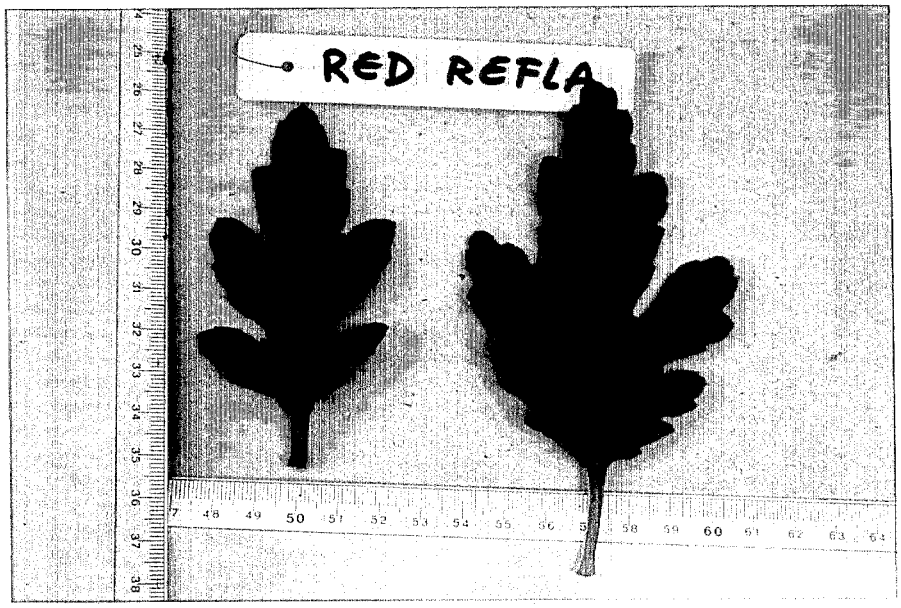
RED REFLA.
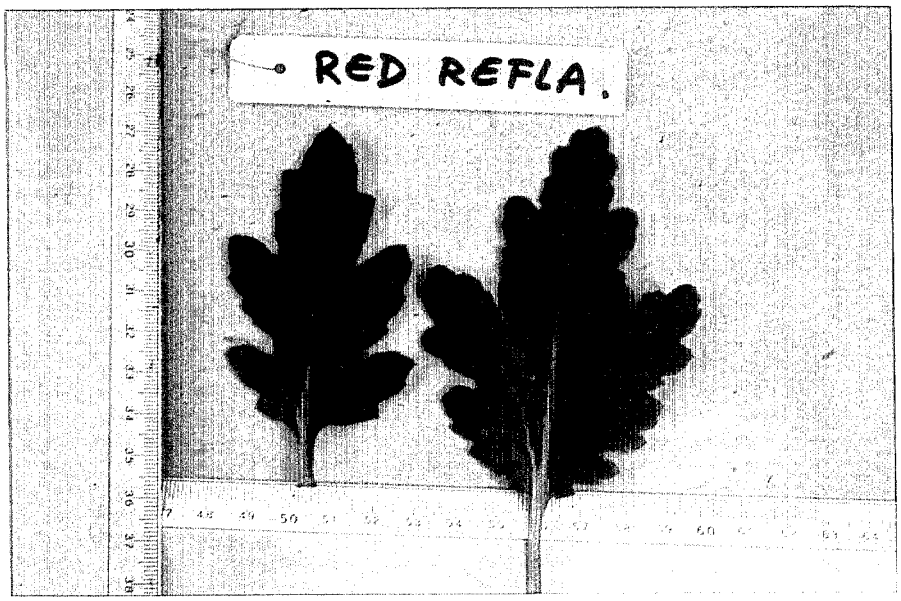
RED REFLA.